US009765405B2

(12) United States Patent
Hyldig-Nielsen et al.

(10) Patent No.: US 9,765,405 B2
(45) Date of Patent: Sep. 19, 2017

(54) **PNA PROBES, PROBE SETS, METHODS AND KITS PERTAINING TO THE DETECTION OF *CANDIDA***

(71) Applicant: APPLIED BIOSYSTEMS, LLC, Carlsbad, CA (US)

(72) Inventors: Jens J. Hyldig-Nielsen, Hillerod (DK); Henrik Stender, Gentofte (DK); Kenneth M. Oliveira, Newton, MA (US); Susan Rigby, Acton, MA (US)

(73) Assignee: Applied Biosystems, LLC, Carlsbad, CA (US)

( * ) Notice: Subject to any disclaimer, the term of this patent is extended or adjusted under 35 U.S.C. 154(b) by 116 days.

(21) Appl. No.: 14/571,080

(22) Filed: Dec. 15, 2014

(65) Prior Publication Data

US 2015/0176086 A1 Jun. 25, 2015

Related U.S. Application Data

(63) Continuation of application No. 13/207,283, filed on Aug. 10, 2011, now Pat. No. 8,912,312, which is a continuation of application No. 10/150,045, filed on May 17, 2002, now Pat. No. 8,026,051.

(60) Provisional application No. 60/292,147, filed on May 18, 2001.

(51) Int. Cl.
*C12Q 1/68* (2006.01)
*C07K 14/00* (2006.01)

(52) U.S. Cl.
CPC .......... *C12Q 1/6895* (2013.01); *C07K 14/003* (2013.01); *C12Q 1/689* (2013.01); *C12Q 2525/107* (2013.01)

(58) Field of Classification Search
None
See application file for complete search history.

(56) References Cited

U.S. PATENT DOCUMENTS

| | | | | |
|---|---|---|---|---|
| 5,595,874 | A | * | 1/1997 | Hogan ............... C12Q 1/6811 435/6.12 |
| 5,707,802 | A | * | 1/1998 | Sandhu ............... C07K 14/37 435/270 |
| 5,708,159 | A | | 1/1998 | Ohno et al. |
| 5,925,517 | A | * | 7/1999 | Tyagi ............... C12Q 1/6816 435/6.1 |
| 6,046,006 | A | | 4/2000 | Einsele et al. |
| 6,280,946 | B2 | | 8/2001 | Hyldig-Nielsen et al. |
| 2003/0165833 | A1 | * | 9/2003 | Hogan ............... C12Q 1/6895 435/6.15 |

FOREIGN PATENT DOCUMENTS

| | | |
|---|---|---|
| DE | 19955303 | 5/2001 |
| EP | 0422869 | 4/1991 |
| JP | 08-089254 | 12/2000 |
| WO | WO 99/21881 | * 5/1999 ............ C07H 21/04 |
| WO | WO-99/21881 | 5/1999 |
| WO | WO-00/77259 | 12/2000 |

OTHER PUBLICATIONS

Wong et al. (Genbank Accession No. X51831, Sep. 1998).*
Buchardt et al. (Trends in Biotechnology, vol. 11, No. 9, pp. 384-386, 1993).*
02726881.2, "European Search Report dated Jul. 4, 2006", 5 pages.
02726881.2, "Partial European Search Report dated Apr. 19, 2006", 4 pages.
Buchardt, et al., *Trends in Biotechnology*, vol. 11, No. 9, 1993, pp. 384-386.
Egholm, M. et al., "PNA hybridizes to complementary oligonucleotides obeying the Watson-Crick", *Nature*, 1993, 365, 566-568.
Elie, C. M. et al., "Rapid Identification of *Candida* species with species-specific DNA probes", *J. Clin. Microbiol.*, vol. 36, 1998, 3260-5.
Gilfillan, et al., "Genbank Accession No. X99399, May 1998".
Guiver, M. et al., "Rapid Identification of *Candida* species by TaqMan PCR", *J. Clin. Pathol.*, vol. 54, 2001, 362-6.
Guo, Z. et al., "Enhanced discrimination of a single nucleotide polymorphisms by artificial mismatch hybridization", *Nature Biotechnology*, 15, 1997, 331-335.
Haynes, et al., "Rapid Identification of Candida albicans, C. glabrata, C. parapsilosis and C. krusei by species-specific PCR of large subunit ribosomal DNA", *J. Med. Microbiol.*, vol. 44, 1996, 390-6.
Hendriks, et al., "Genbank Accession No. M55528, Apr. 1993".
Kempf, et al., "Fluorescent in situ hybridization allows rapid Indentification of microorganisms in blood cultures", *J. Clin. Microbiol.*, vol. 38, 2000, 830-838.

(Continued)

*Primary Examiner* — Jeanine A Goldberg

(57) ABSTRACT

This invention is related to novel PNA probes, probe sets, methods and kits pertaining to the detection of one or more species of *Candida* yeast. Non-limiting examples of probing nucleobase sequences that can be used for the probes of this invention can be selected from the group consisting of: AGA-GAG-CAG-CAT-GCA (Seq. Id. No. 1), AGA-GAG-CAA-CAT-GCA (Seq. Id. No. 2), ACA-GCA-GAA-GCC-GTG (Seq. Id. No. 3), CAT-AAA-TGG-CTA-CCA-GA (Seq. Id. No. 4), CAT-AAA-TGG-CTA-CCC-AG (Seq. Id. No. 5), ACT-TGG-AGT-CGA-TAG (Seq. Id. No. 6), CCA-AGG-CTT-ATA-CTC-GC (Seq. Id. No. 7), CCC-CTG-AAT-CGG-GAT (Seq. Id. No. 8), GAC-GCC-AAA-GAC-GCC (Seq. Id. No. 9), ATC-GTC-AGA-GGC-TAT-AA (Seq. Id. No. 10), TAG-CCA-GAA-GAA-AGG (Seq. Id. No. 11), CAT-AAA-TGG-CTA-GCC-AG (Seq. Id. No. 12), CTC-CGA-TGT-GAC-TGC-G (Seq. Id. No. 13), TCC-CAG-ACT-GCT-CGG (Seq. Id. No. 14), TCC-AAG-AGG-TCG-AGA (Seq. Id. No. 15), GCC-AAG-CCA-CAA-GGA (Seq. Id. No. 16), GCC-GCC-AAG-CCA-CA (Seq. Id. No. 17), GGA-CTT-GGG-GTT-AG (Seq. Id. No. 18), CCG-GGT-GCA-TTC-CA (Seq. Id. No. 19), ATG-TAG-AAC-GGA-ACT-A (Seq. Id. No. 20), GAT-TCT-CGG-CCC-CAT-G (Seq. Id. No. 21), CTG-GTT-CGC-CAA-AAA-G (Seq. Id. No. 22) and AGT-ACG-CAT-CAG-AAA (Seq. Id. No. 23).

20 Claims, 1 Drawing Sheet

(56) References Cited

OTHER PUBLICATIONS

Kurtzman, C. P., "Identification and phylogeny of ascomycetous yeasts from analysis of nuclear large subunit (26S) ribosomal DNA partial sequences", *Antonie Van Leeuwenhoek*, vol. 73, 1998, 331-371.

Lischewski, A. et al., "Detection and Identification of *Candida* species in experimentally Infected tissue and human blood by rRNA-specific fluorescent In situ hybridization", *J. Clin. Microbiol.*, vol. 35, 1997, 2943-8.

Lischewski, A. et al., "Specific detection of Candida albicans and Candida tropicalis by fluorescent in situ hybridization with an 18S rRNA-targeted oligonucleotide probe", *Microbiology*, vol. 142, 1996, 2731-40.

Mannarelli, B. M. et al., "Rapid Identification of Candida albicans and other human pathogenic yeast by using short oligonucleotides in a PCR", *J. Clin. Microbiol.*, vol. 36, 1998, 1634-1641.

Nielsen, et al., "Peptide Nucleic Acids (PNA). Potential Anti-Sense and Anti-Gene Agents", *Anticancer Drug Des.*, vol. 8(1), 1993, 53-63.

Perry-O'Keefe, H. et al., "Identification of Indicator microorganisms using a standardized PNA FISH method", *J Microbiol. Methods*, 47(3), 2001, 281-292.

Oliveira, K. et al., "Differentiation of Candida Albicans and Candida Dubliniensis by Fluorescent In Situ", *Journal of Clinical Microbiology*, 2001, 11, 4138-4141.

Park, S.M. et al., "Rapid Identification of Candida dubliniensis using a species-specific molecular beacon", *J. Clin. Microbiol.* 38(8), 2000, 2829-2836, 47(3), 2001, 281-292.

Perry-O'Keefe, H., et al., "Filter-based PNA in situ hybridization for rapid detection, identification and enumeration of specific micro-organisms", *Journal of Applied Microbiology*, vol. 90, No. 2, Feb. 2001, pp. 180-189.

Pfaller, M. A. et al., "International surveillance of bloodstream Infections due to *Candida* species: Frequency of occurance and In vitro susceptibilities to fluconazole, ravuconazole, and voriconazole of Isolates collected from 1997 through 1999 in the SENTRY antimicrobial Survei", *J. Clin. Microbiol.*, vol. 39, 3254-3259.

Shin, J. H. et al., "Rapid Identification of *Candida* species in blood cultures by clinically useful PCR method", *J. Clin. Microbiol.*, vol. 35, 1997, 1454-1459.

Stender, H. et al., "Identification of Dekkera bruxeilensis (Brettanomyces) from wine by fluorescence In situ hybridization using peptide nucleic acid probes", *Appl. Environ. Microbiol.*, vol. 67, 2001, 938-941.

Sugita, et al., "Genbank Accession No. AB013588, Dec. 1999".

Sugita, et al., "Genbank Accession No. AB031586".

Tomac, S. et al., "Ionic effects on the stability and conformation of peptide nucleic acid complexes.", *J. Am. Chem. Soc.*; vol. 118, 1996, 5544-5552.

Weiler, J. et al., "Hybridisation based DNA screening on peptide nucleic acid (PNA) oligomer arrays.", *Nucl. Acids Res.*; vol. 25, 1997, 2792-2799.

Wong, et al., "Genbank Accession No. X51831, Sep. 1998".

\* cited by examiner

PNA FISH with Can26S03
*C. albicans*
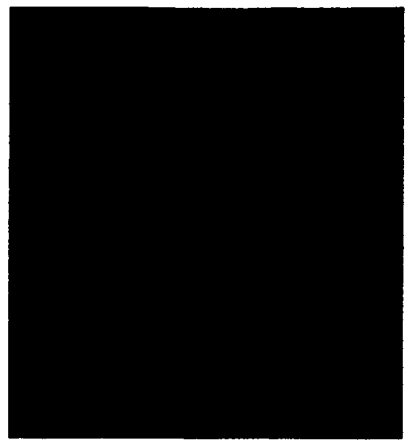
*C. dubliniensis*
*C. glabrata*
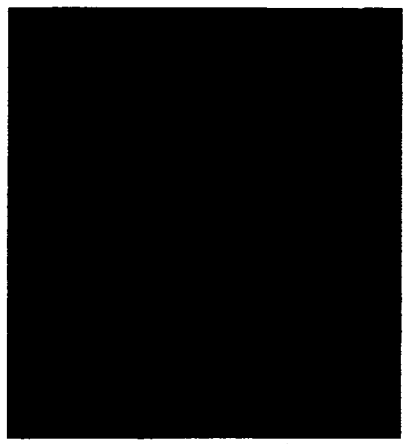
*C. tropicalis*
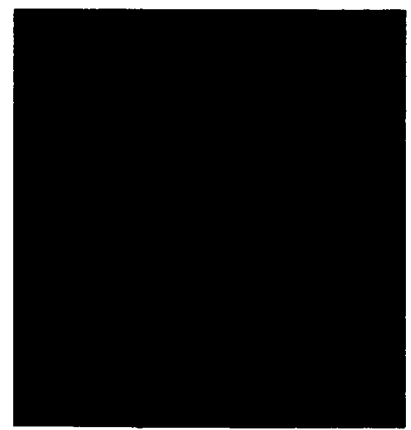
*S. cerevisiae*

SEQUENCE LISTING

```
<160> NUMBER OF SEQ ID NOS: 23

<210> SEQ ID NO 1
<211> LENGTH: 15
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 1
agagaccagc atgca                                                      15

<210> SEQ ID NO 2
<211> LENGTH: 15
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 2
agagagcaac atgca                                                      15

<210> SEQ ID NO 3
<211> LENGTH: 15
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 3
acagcagaag ccgtg                                                      15

<210> SEQ ID NO 4
<211> LENGTH: 17
<212> TYPE: DNA
<213> ORGANISM: Candida
```

```
<220> FEATURE:
<223> OTHER INFORMATION: Description of Combined DNA/RNA Molecule:
      Probing Nucleobase Sequence of PNA Probe

<400> SEQUENCE: 4
cataaatggc taccaga                                                    17

<210> SEQ ID NO 5
<211> LENGTH: 17
<212> TYPE: DNA
<213> ORGANISM: Candida
<220> FEATURE:
<223> OTHER INFORMATION: Description of Combined DNA/RNA Molecule:
      Probing Nucleobase Sequence

<400> SEQUENCE: 5
cataaatggc tacccag                                                    17

<210> SEQ ID NO 6
<211> LENGTH: 15
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 6
acttggagtc gatag                                                      15

<210> SEQ ID NO 7
<211> LENGTH: 17
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 7
ccaaggctta tactcgc                                                    17

<210> SEQ ID NO 8
<211> LENGTH: 15
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 8
cccctgaatc gggat                                                      15

<210> SEQ ID NO 9
<211> LENGTH: 15
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 9
gacgccaaag acgcc                                                      15

<210> SEQ ID NO 10
<211> LENGTH: 17
<212> TYPE: DNA
<213> ORGANISM: Candida
<220> FEATURE:
```

```
<223> OTHER INFORMATION: Description of Combined DNA/RNA Molecule:
      Probing Nucleobase Sequence of PNA Probe

<400> SEQUENCE: 10
atcgtcagag gctataa                                                        17

<210> SEQ ID NO 11
<211> LENGTH: 15
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 11
tagccagaag aaagg                                                          15

<210> SEQ ID NO 12
<211> LENGTH: 17
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 12
cataaatggc tagccag                                                        17

<210> SEQ ID NO 13
<211> LENGTH: 16
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 13
ctccgatgtg actgcg                                                         16

<210> SEQ ID NO 14
<211> LENGTH: 15
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 14
tcccagactg ctcgg                                                          15

<210> SEQ ID NO 15
<211> LENGTH: 15
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 15
tccaagaggt cgaga                                                          15

<210> SEQ ID NO 16
<211> LENGTH: 15
<212> TYPE: DNA
<213> ORGANISM: Candida
<220> FEATURE:
<223> OTHER INFORMATION: Description of Combined DNA/RNA Molecule:
```

-continued

Probing Nucleobase Sequence of PNA Probe

<400> SEQUENCE: 16
gccaagccac aagga                                                    15

<210> SEQ ID NO 17
<211> LENGTH: 14
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 17
gccgccaagc caca                                                     14

<210> SEQ ID NO 18
<211> LENGTH: 14
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 18
ggacttgggg ttag                                                     14

<210> SEQ ID NO 19
<211> LENGTH: 14
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 19
ccgggtgcat tcca                                                     14

<210> SEQ ID NO 20
<211> LENGTH: 16
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 20
atgtagaacg gaacta                                                   16

<210> SEQ ID NO 21
<211> LENGTH: 16
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 21
gattctcggc cccatg                                                   16

<210> SEQ ID NO 22
<211> LENGTH: 16
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

```
<400> SEQUENCE: 22
ctggttcgcc aaaaag                                                    16

<210> SEQ ID NO 23
<211> LENGTH: 15
<212> TYPE: DNA
<213> ORGANISM: Candida
<220> FEATURE:
<223> OTHER INFORMATION: Description of Combined DNA/RNA Molecule:
      Probing Nucleobase Sequence of PNA Probe

<400> SEQUENCE: 23
agtacgcatc agaaa                                                     15
```

PNA PROBES, PROBE SETS, METHODS AND KITS PERTAINING TO THE DETECTION OF CANDIDA

CROSS REFERENCE TO RELATED APPLICATIONS

This application is a continuation of U.S. application Ser. No. 13/207,283, filed Aug. 20, 2011, now U.S. Pat. No. 8,912,312, which is a continuation of U.S. application Ser. No. 10/150,045, filed May 17, 2002, now U.S. Pat. No. 8,026,051, which claims the benefit of U.S. Provisional Application No. 60/292,147 filed on May 18, 2001; each of which disclosures are herein incorporated by reference in their entirety.

STATEMENT REGARDING FEDERALLY SPONSORED RESEARCH OR DEVELOPMENT

The US Government has certain rights in this invention as provided for by the terms of the Cooperative Research and Development Agreement (CRADA) No. 58-3K95-8-631 by and between Boston Probes, Inc. and the United States Department of Agriculture.

BACKGROUND OF THE INVENTION

1. Field of the Invention

This invention is related to the field of probe-based detection, analysis and/or quantitation of microorganisms. More specifically, this invention relates to novel PNA probes, probe sets, methods and kits pertaining for the detection, identification and/or enumeration of organisms of the various species of the *Candida* genus.

2. Description of the Related Art

Nucleic acid hybridization is a fundamental process in molecular biology. Probe-based assays are useful in the detection, quantitation and/or analysis of nucleic acids. Nucleic acid probes have long been used to analyze samples for the presence of nucleic acid from bacteria, fungi, virus or other organisms and are also useful in examining genetically-based disease states or clinical conditions of interest. Nonetheless, probe-based assays have been slow to achieve commercial success. This lack of commercial success is, at least partially, the result of difficulties associated with specificity, sensitivity and reliability.

Despite its name, Peptide Nucleic Acid (PNA) is neither a peptide, a nucleic acid nor is it an acid. Peptide Nucleic Acid (PNA) is a non-naturally occurring polyimide that can hybridize to nucleic acid (DNA and RNA) with sequence specificity (See: U.S. Pat. No. 5,539,082 and Egholm et al., *Nature* 365: 566-568 (1993)). Being a non-naturally occurring molecule, unmodified PNA is not known to be a substrate for the enzymes that are known to degrade peptides or nucleic acids. Therefore, PNA should be stable in biological samples, as well as have a long shelf-life. Unlike nucleic acid hybridization, which is very dependent on ionic strength, the hybridization of a PNA with a nucleic acid is fairly independent of ionic strength and is favored at low ionic strength, conditions that strongly disfavor the hybridization of nucleic acid to nucleic acid (Egholm et al., *Nature, at p.* 567). The effect of ionic strength on the stability and conformation of PNA complexes has been extensively investigated (Tomac et al., *J. Am. Chem. Soc.* 118:55 44-5552 (1996)). Sequence discrimination is more efficient for PNA recognizing DNA than for DNA recognizing DNA (Egholm et al., *Nature, at p.* 566). However, the advantages in point mutation discrimination with PNA probes, as compared with DNA probes, in a hybridization assay, appears to be somewhat sequence dependent (Nielsen et al., *Anti-Cancer Drug Design* 8:53-65, (1993) and Weiler et al., *Nucl. Acids Res.* 25: 2792-2799 (1997)).

Though they hybridize to nucleic acid with sequence specificity (See: Egholm et al., *Nature, at p.* 567), PNAs have been slow to achieve commercial success at least partially due to cost, sequence specific properties/problems associated with solubility and self-aggregation (See: Bergman, F., Bannwarth, W. and Tam, S., *Tett. Lett.* 36:6823-6826 (1995), Haaima, G., Lohse, A., Buchardt, O. and Nielsen, P. E., *Angew. Chem. Int. Ed. Engl.* 35:1939-1942 (1996) and Lesnik, E., Hassman, F., Barbeau, J., Teng, K. and Weiler, K., *Nucleosides & Nucleotides* 16:1775-1779 (1997) at p 433, col. 1, ln. 28 through col. 2, ln. 3) as well as the uncertainty pertaining to non-specific interactions that might occur in complex systems such as a cell (See: Good, L. et al., *Antisense & Nucleic Acid Drug Development* 7:431-437 (1997)). However, problems associated with solubility and self-aggregation have been reduced or eliminated (See: Gildea et al., *Tett. Lett,* 39: 7255-7258 (1998)). Nevertheless, their unique properties clearly demonstrate that PNA is not the equivalent of a nucleic acid in either structure or function. Consequently, PNA probes should be evaluated for performance and optimization to thereby confirm whether they can be used to specifically and reliably detect a particular nucleic acid target sequence, particularly when the target sequence exists in a complex sample such as a cell, tissue or organism.

SUMMARY OF THE INVENTION

This invention is directed to PNA probes, probe sets, methods and kits useful for detecting, identifying and/or quantitating *Candida* yeast in a sample. The PNA probes, probe sets, methods and kits of this invention are suitable for the analysis of nucleic acid, whether or not it is present within an organism of interest. Accordingly, this invention can be used for both the analysis of organisms or for the analysis of nucleic acid extracted from or derived from an organism of interest.

Generally, this invention can be particularly useful for the determination of particular species of the *Candida* genus. The PNA probes and probe sets of this invention comprise probing nucleobase sequences that are particularly useful for the specific detection of certain species of *Candida*, including *C. albicans* (also comprising *C. stellatoidea*, a biovar of *C. albicans*), *C. dubliniensis, C. krusei, C. glabrata, C. parapsilosis* and *C. tropicalis*. A particularly useful probing nucleobase sequence is Seq. Id. No. 1 (See: Table 1) because it can be highly specific for *C. albicans*, a pathogen that is particularly important to determine as early as possible in the area of blood culture analysis. Exemplary probing nucleobase sequences for the probes of this invention are listed in Table 1, below. The species of *Candida* for which each probe is intended to determine is also listed in the Table.

This invention is further directed to a method suitable for detecting, identifying and/or quantitating a species of *Candida* in a sample. For example, the method can be directed to the detection of a particular species of *Candida* wherein the species is selected from the group consisting of: *C. albicans, C. dubliniensis, C. krusei, C. glabrata, C. parapsilosis* and *C. tropicalis*.

The method can comprise contacting the sample with one or more PNA probes, wherein suitable probes are described herein. According to the method, the presence, absence and/or number of the one or more species of *Candida* in the sample is then detected, identified and/or quantitated. Detection, identification and/or quantitation is made possible by correlating the hybridization, under suitable hybridization conditions or suitable in-situ hybridization conditions, of the probing nucleobase sequence of a PNA probe to the target sequence with the presence, absence and/or quantity of target organism in the sample. This correlation is made possible by direct or indirect determination of the probe/target sequence hybrid.

In yet another embodiment, this invention is directed to kits suitable for performing an assay that determines the presence, absence and/or quantity of a species of *Candida* in a sample. The kits of this invention comprise one or more PNA probes and other reagents or compositions that are selected to perform an assay or otherwise simplify the performance of an assay.

The PNA probes, probe sets, methods and kits of this invention have been demonstrated to be relatively specific for the species of *Candida* for which they are intended to determine. Moreover, the assays described herein are rapid (2-3 hours or less), sensitive, reliable and capable, in a single assay, of identification as well as detection and/or enumeration of the organisms listed in Table 1.

The PNA probes, probe sets, methods and kits of this invention can be particularly useful for the determination of *Candida* in food, beverages, water, pharmaceutical products, personal care products, dairy products and/or environmental samples. The analysis of beverages includes soda, bottled water, fruit juice, beer, wine or liquor products. Suitable PNA probes, probe sets, methods and kits can be particularly useful for the analysis of raw materials, equipment, products or processes used to manufacture or store food, beverages, water, pharmaceutical products, personal care products dairy products or for the analysis of environmental samples.

Additionally, the PNA probes, probe sets, methods and kits of this invention can be particularly useful for the detection of *Candida* species in clinical samples and clinical environments. By way of a non-limiting example, the PNA probes, probe sets, methods and kits of this invention can be particularly useful in the analysis of blood cultures or in samples derived therefrom (e.g. subcultures). Other non-limiting examples of clinical samples include: sputum, laryngeal swabs, gastric lavage, bronchial washings, biopsies, aspirates, expectorates, body fluids (e.g. spinal, pleural, pericardial, synovial, blood, pus, amniotic, and urine), bone marrow and tissue sections (including cultures and subcultures derived therefrom). Suitable PNA probes, probe sets, methods and kits will also be particularly useful for the analysis of clinical specimens, equipment, fixtures or products used to treat humans or animals.

BRIEF DESCRIPTION OF THE DRAWINGS

FIG. 1 comprises 5 images that were obtained using a fluorescent microscope using a FITC/Texas red filter for five culture samples, each culture sample representing a different species of *Candida*, wherein all samples have been treated with the PNA probe Can26S03 having sequence Id No. 1 as the probing nucleobase sequence. Only the sample containing *C. albicans* is positive thereby demonstrating that the probe is highly specific for *C. albicans* and can be used to distinguish numerous other *Candida* species, including the difficult to distinguish, *C. dubliniensis*.

DETAILED DESCRIPTION OF THE INVENTION

1. Definitions:

a. As used herein, "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobase include those nucleobases illustrated in FIGS. 2(A) and 2(B) of Buchardt et al. of U.S. Pat. No. 6,357,163 (incorporated herein by reference).

b. As used herein, "nucleobase sequence" means any segment, or aggregate of two or more segments of a polymer that comprises nucleobase-containing subunits. Non-limiting examples of suitable polymers include oligodeoxynucleotides (e.g. DNA), oligoribonucleotides (e.g. RNA), peptide nucleic acids (PNA), PNA chimeras, PNA oligomers, nucleic acid analogs and/or nucleic acid mimics.

c. As used herein, "target sequence" is a nucleobase sequence of a polynucleobase strand sought to be determined. The target sequence can be a subsequence of the rRNA of *Candida* yeast.

d. As used herein, "polynucleobase strand" means a complete single polymer strand comprising nucleobase subunits.

e. As used herein, "nucleic acid" is a nucleobase sequence-containing polymer, or polynucleobase strand, having a backbone formed from nucleotides, or analogs thereof. Preferred nucleic acids are DNA and RNA. For the avoidance of any doubt, PNA is a nucleic acid mimic and not a nucleic acid analog.

f. As used herein, "peptide nucleic acid" or "PNA" means any oligomer or polymer segment comprising two or more PNA subunits (residues), including, but not limited to, any of the oligomer or polymer segments referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470 and 6,357,163; all of which are herein incorporated by reference. The term "peptide nucleic acid" or "PNA" shall also apply to any oligomer or polymer segment comprising two or more subunits of those nucleic acid mimics described in the following publications: Lagriffoul et at, *Bioorganic & Medicinal Chemistry Letters*, 4: 1081-1082 (1994); Petersen et al., *Bioorganic & Medicinal Chemistry Letters*, 6: 793-796 (1996); Diderichsen et al., *Tett. Lett.* 37: 475-478 (1996); Fujii et al., *Bioorg. Med. Chem. Lett.* 7: 637-627 (1997); Jordan et. al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Diederichsen, U., *Bioorganic & Medicinal Chemistry Letters*, 7:1743-1746 (1997); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin. Trans.* 1 1:5 55-560 (1997); Howarth et al., *J. Org. Chem.* 62: 5441-5450 (1997); Altmann, K-H et al., *Bioorganic & Medici-* nal Chemistry Letters, 7: 1119-1122 (1997); Diederichsen, U., Bioorganic & Med. Chem. Lett., 8: 165-168 (1998); Diederichsen et al., Angew. Chem. Int. Ed., 37: 302-305 (1998); Cantin et al., Tett. Lett., 38: 4211-4214 (1997); Ciapetti et al., Tetrahedron, 53: 1167-1176 (1997); Lagriffoule et al., Chem. Eur. J., 3: 912-919 (1997); Kumar et at, Organic Letters 3(9): 1269-1272 (2001); and the Peptide-Based Nucleic Acid Mimics (PENAMs) of Shah et al. as disclosed in WO96/04000.

In certain embodiments, a "peptide nucleic acid" or "PNA" is an oligomer or polymer segment comprising two or more covalently linked subunits of the formula:

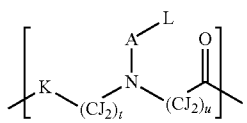

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each R' is the same or different and is an alkyl group having one to five carbon atoms that may optionally contain a heteroatom or a substituted or unsubstituted aryl group. Each. A is selected from the group consisting of a single bond, a group of the formula; $-(CJ_2)_s$- and a group of the formula; $-(CJ_2)_sC(O)-$, wherein, J is defined above and each s is a whole number from one to five. Each t is 1 or 2 and each u is 1 or 2. Each L is the same or different and is independently selected from: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine), other naturally occurring nucleobase analogs or other non-naturally occurring nucleobases.

In certain other embodiments, a PNA subunit consists of a naturally occurring or non-naturally occurring nucleobase attached to the N-α-glycine nitrogen of the N-[2-(aminoethyl)]glycine backbone through a methylene carbonyl linkage; this currently being the most commonly used form of a peptide nucleic acid subunit.

g. As used herein, the terms "label", "reporter moiety" or "detectable moiety" are interchangeable and refer to moieties that can be attached to PNA oligomer or antibody, or otherwise be used in a reporter system, to thereby render the oligomer or antibody detectable by an instrument or method. For example, a label can be any moiety that: (i) provides a detectable signal; (ii) interacts with a second label to modify the detectable signal provided by the first or second label; or (iii) confers a capture function, i.e. hydrophobic affinity, antibody/antigen, ionic complexation.

h. As used herein, "sequence specifically" means hybridization by base pairing through hydrogen bonding. Non-limiting examples of standard base pairing includes adenine base pairing with thymine or uracil and guanine base pairing with cytosine. Other non-limiting examples of base-pairing motifs include, but are not limited to: adenine base pairing with any of: 5-propynyl-uracil, 2-thio-5-propynyl-uracil, 2-thiouracil or 2-thiothymine; guanine base pairing with any of: 5-methylcytosine or pseudoisocytosine; cytosine base pairing with any of: hypoxanthine, N9-(7-deaza-guanine) or N9-(7-deaza-8-aza-guanine); thymine or uracil base pairing with any of: 2-aminopurine, N9-(2-amino-6-chloropurine) or N9-(2,6-diaminopurine); and N8-(7-deaza-8-aza-adenine), being a universal base, base pairing with any other nucleobase, such as for example any of: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine) or N9-(7-deaza-8-aza-guanine) (See: Seela et al., Nucl. Acids, Res.: 28(17): 3224-3232 (2000)).

i. As used herein, the term "chimera" or "chimeric oligomer" means an oligomer comprising two or more linked subunits that are selected from different classes of subunits. For example, a PNA/DNA chimera would comprise at least two PNA subunits linked to at least one 2'-deoxyribonucleic acid subunit (For exemplary methods and compositions related to PNA/DNA chimera preparation See: WO96/40709). Exemplary component subunits of the chimera are selected from the group consisting of PNA subunits, naturally occurring amino acid subunits, DNA subunits, RNA subunits and subunits of analogues or mimics of nucleic acids.

j. As used herein, the term "linked polymer" means a polymer comprising two or more polymer segments which are linked by a linker. The polymer segments that are linked to form the linked polymer are selected from the group consisting of an oligodeoxynucleotide, an oligoribonucleotide, a peptide, a polyimide, a peptide nucleic acid (PNA) and a chimera.

k. As used herein "solid support" or "solid carrier" means any solid phase material upon which a oligomer is synthesized, attached, ligated or otherwise immobilized. Solid support encompasses terms such as "resin", "solid phase", "surface" and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, a get, or a surface. Surfaces may be planar, substantially planar, or non-planar. Solid supports may be porous or non-porous, and may have swelling, or non-swelling characteristics. A solid support may be configured in the form of a well, depression or other container, vessel, feature or location. A plurality of solid supports may be configured in an array at various locations, addressable for robotic delivery of reagents, or by detection means including scanning by laser illumination and confocal or deflective light gathering.

l. As used herein, "support bound" means immobilized on or to a solid support. It is understood that immobilization can occur by any means, including for example; by covalent attachment, by electrostatic immobilization, by attachment through a ligand/ligand interaction, by contact or by depositing on the surface.

2. Description

I. General:

PNA Synthesis:

Methods for the chemical assembly of PNAs are well known (See: U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470; all of which are herein incorporated by reference (Also see: PerSeptive Biosystems Product Literature)). As a general reference for PNA synthesis methodology also please see: Nielsen et al., *Peptide Nucleic Acids; Protocols and Applications,* Horizon Scientific Press, Norfolk England (1999).

Chemicals and instrumentation for the support bound automated chemical assembly of peptide nucleic acids are now commercially available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus that can be condensed with the next synthon to be added to the growing polymer. Because standard peptide chemistry is utilized, natural and non-natural amino acids can be routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

PNA Labeling:

Non-limiting methods for labeling PNAs are described in U.S. Pat. No. 6,110,676, U.S. Pat. No. 6,361,942, U.S. Pat. No. 6,355,421 (all incorporated herein by reference), WO99/21881, the examples section of this specification or are otherwise well known in the art of PNA synthesis. Other non-limiting examples for labeling PNAs are also discussed in Nielsen et al., *Peptide Nucleic Acids; Protocols and Applications,* Horizon Scientific Press, Norfolk England (1999).

Labels:

Non-limiting examples of detectable moieties (labels) that can be used to label PNA probes or antibodies used in the practice of this invention can include a dextran conjugate, a branched nucleic acid detection system, a chromophore, a fluorophore, a spin label, a radioisotope, an enzyme, a hapten, an acridinium ester or a chemiluminescent compound. Other suitable labeling reagents and preferred methods of attachment would be recognized by those of ordinary skill in the art of PNA, peptide or nucleic acid synthesis.

Non-limiting examples of haptens include 5(6)-carboxyt-luorescein, 2,4-dinitrophenyl, digoxigenin, and biotin.

Non-limiting examples of fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.).

Non-limiting examples of enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP), soy bean peroxidase (SBP)), ribonuclease and protease.

Energy Transfer

In one embodiment, PNA oligomers can be labeled with an energy transfer set. For energy transfer to be useful in determining hybridization, there should be an energy transfer set comprising at least one energy transfer donor and at least one energy transfer acceptor moiety. Often, the energy transfer set will include a single donor moiety and a single acceptor moiety, but this is not a limitation. An energy transfer set may contain more than one donor moiety and/or more than one acceptor moiety. The donor and acceptor moieties operate such that one or more acceptor moieties accept energy transferred from the one or more donor moieties or otherwise quench the signal from the donor moiety or moieties. Thus, in one embodiment, both the donor moiety(ies) and acceptor moiety(ies) are fluorophores. Though the previously listed fluorophores (with suitable spectral properties) might also operate as energy transfer acceptors, the acceptor moiety can also be a non-fluorescent quencher moiety such as 4-((-4-(dimethylamino)phenyl) azo)benzoic acid (dabcyl). The labels of the energy transfer set can be linked at the oligomer termini or linked at a site within the oligomer. For example, each of two labels of an energy transfer set can be linked at the distal-most termini of the oligomer.

Transfer of energy between donor and acceptor moieties may occur through any energy transfer process, such as through the collision of the closely associated moieties of an energy transfer set(s) or through a non-radiative process such as fluorescence resonance energy transfer (FRET). For FRET to occur, transfer of energy between donor and acceptor moieties of a energy transfer set requires that the moieties be close in space and that the emission spectrum of a donor(s) have substantial overlap with the absorption spectrum of the acceptor(s) (See: Yaron et al. *Analytical Biochemistry,* 95: 228-235 (1979) and particularly page 232, col. 1 through page 234, col. 1). Alternatively, collision mediated (radiationless) energy transfer may occur between very closely associated donor and acceptor moieties whether or not the emission spectrum of a donor moiety(ies) has a substantial overlap with the absorption spectrum of the acceptor moiety(ies) (See: Yaron et al., *Analytical Biochemistry,* 95: 228-235 (1979) and particularly page 229, col. 1 through page 232, col. 1). This process is referred to as intramolecular collision since it is believed that quenching is caused by the direct contact of the donor and acceptor moieties (See: Yaron et al.). It is to be understood that any reference to energy transfer in the instant application encompasses all of these mechanistically distinct phenomena. It is also to be understood that energy transfer can occur though more than one energy transfer process simultaneously and that the change in detectable signal can be a measure of the activity of two or more energy transfer processes. Accordingly, the mechanism of energy transfer is not a limitation of this invention.

Detecting Energy Transfer in a Self-Indicating PNA Oligomer:

When labeled with an energy transfer set, we refer to the PNA oligomer as being self-indicating. In one embodiment, a self-indicating PNA oligomer can be labeled in a manner that is described in co-pending and commonly owned patent application U.S. Ser. No. 09/179,162 (now allowed), entitled: "Methods, Kits And Compositions Pertaining To Linear Beacons" and the related PCT application which has also now published as WO99/21881, both of which are hereby incorporated by reference.

Hybrid formation between a self-indicating oligomer and a target sequence can be monitored by measuring at least one physical property of at least one member of the energy transfer set that is detectably different when the hybridization complex is formed as compared with when the oligomer exists in a non-hybridized state. We refer to this phenomenon as the self-indicating property of the oligomer. This change in detectable signal results from the change in efficiency of energy transfer between donor and acceptor moieties caused by hybridization of the oligomer to the target sequence.

For example, the means of detection can involve measuring fluorescence of a donor or acceptor fluorophore of an energy transfer set. In one embodiment, the energy transfer set may comprise at least one donor fluorophore and at least one acceptor (fluorescent or non-fluorescent) quencher such that the measure of fluorescence of the donor fluorophore can be used to detect, identify or quantitate hybridization of the oligomer to the target sequence. For example, there may be a measurable increase in fluorescence of the donor fluorophore upon the hybridization of the oligomer to a target sequence.

In another embodiment, the energy transfer set comprises at least one donor fluorophore and at least one acceptor fluorophore such that the measure of fluorescence of either, or both, of at least one donor moiety or one acceptor moiety can be used to can be used to detect, identify or quantitate hybridization of the oligomer to the target sequence.

Self-indicating PNA oligomers can be used in in-situ hybridization assays. However, certain self-indicating PNA oligomers are particularly well suited for the analysis of nucleic acid amplification reactions (e.g. PCR) either in real-time or at the end point (See: WO99/21881).

Determining Energy Transfer in a Detection Complex:

In another embodiment, the PNA oligomers of the present invention are labeled solely with a quencher moiety and can be used as a component oligomer in a Detection Complex as more fully explained in U.S. Pat. No. 6,361,942, entitled: "Methods, Kits And Compositions Pertaining To Detection Complexes", herein incorporated by reference. When the Detection Complex is formed, at least one donor moiety of one component polymer is brought sufficiently close in space to at least one acceptor moiety of a second component polymer. Since the donor and acceptor moieties of the set are closely situated in space, transfer of energy occurs between moieties of the energy transfer set. When the Detection Complex dissociates, as for example when one of the component polymers of the Detection Complex hybridizes to a target sequence, the donor and acceptor moieties do not interact sufficiently to cause substantial transfer of energy from the donor and acceptor moieties of the energy transfer set and there is a correlating change in detectable signal from the donor and/or acceptor moieties of the energy transfer set. Consequently, Detection Complex formation/dissociation can be determined by measuring at least one physical property of at least one member of the energy transfer set that is detectably different when the complex is formed as compared with when the component polymers of the Detection Complex exist independently and unassociated.

Detectable and Independently Detectable Moieties/Multiplex Analysis:

A multiplex hybridization assay can be performed in accordance with this invention. In a multiplex assay, numerous conditions of interest can be simultaneously examined. Multiplex analysis relies on the ability to sort sample components or the data associated therewith, during or after the assay is completed. In preferred embodiments of the invention, one or more distinct independently detectable moieties can be used to label two or more different probes used in an assay. The ability to differentiate between and/or quantitate each of the independently detectable moieties provides the means to multiplex a hybridization assay because the data that correlates with the hybridization of each of the distinctly (independently) labeled probe to a particular nucleic acid sequence can be correlated with the presence, absence or quantity of each organism sought to be detected in the sample. Consequently, the multiplex assays of this invention can be used to simultaneously detect the presence, absence or quantity of two or more different organisms (e.g. species of *Candida*) in the same sample and in the same assay. For example, a multiplex assay may utilize two or more PNA probes, each being labeled with an independently detectable fluorophore, or a set of independently detectable fluorophores.

Spacer/Linker Moieties:

Generally, spacers are used to minimize the adverse effects that bulky labeling reagents might have on hybridization properties of probes. Linkers typically induce flexibility and randomness into the probe or otherwise link two or more nucleobase sequences of a probe or component polymer. Preferred spacer/linker moieties for the nucleobase polymers of this invention consist of one or more aminoalkyl carboxylic acids (e.g. aminocaproic acid) the side chain of an amino acid (e.g. the side chain of lysine or ornithine), natural amino acids (e.g. glycine), arninooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the probe (For example see: Gildea et al., *Tett. Lett.* 39: 7255-7258 (1998)).

For example, a spacer/linker moiety can comprise one or more linked compounds having the formula: —Y—(O$_m$—(CW$_2$)$_n$)$_o$—Z—. The group Y is selected from the group consisting of: a single bond, —(CW$_2$)$_p$—, —C(O)(CW)$_p$—, —C(S)(CW$_2$)$_p$— and —S(O$_2$)(CW$_2$)$_p$. The group Z has the formula NH, NR$^2$, S or O. Each W is independently H, R$^2$, —OR$^2$, F, Cl, Br or I; wherein, each R$^2$ is independently selected from the group consisting of: —CX$_3$, —CX$_2$CX$_3$, —CX$_2$CX$_2$CX$_3$, —CX$_2$CX(CX$_3$)$_2$, and —C(CX$_3$)$_3$. Each X is independently H, F, Cl, Br or I. Each m is independently 0 or 1. Each n, o and p are independently integers from 0 to 10.

Hybridization. Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination can often be found by the well known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions:

Generally, the more closely related the background causing nucleic acid contaminates are to the target sequence, the more careful stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Aided by no more than routine experimentation and the disclosure provided herein, those of skill in the art will easily be able to determine suitable hybridization conditions for performing assays utilizing the methods, kits and compositions described herein. Suitable in-situ hybridization conditions comprise conditions suitable for performing an in-situ hybridization procedure. Thus, suitable hybridization or suitable in-situ hybridization conditions will become apparent using the disclosure provided herein; with or without additional routine experimentation.

Blocking Probes:

Blocking probes are nucleic acid or non-nucleic acid probes (e.g. PNA probes) that can be used to suppress the binding of the probing nucleobase sequence of the probing polymer to a non-target sequence. Preferred blocking probes are PNA probes (See: Coull et al., WIPO publication No. WO98/24933 as well as U.S. Pat. No. 6,110,676). Typically, blocking probes are closely related to the probing nucleobase sequence and preferably they comprise a point mutation as compared with the probing nucleobase sequence. It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods, kits and compositions of this invention to suppress the binding of the PNA probe to a non-target sequence that might be present and interfere with the performance of the assay. Blocking probes are particularly advantageous in single point mutation discrimination.

Probing Nucleobase Sequence:

The probing nucleobase sequence of a PNA probe is the specific sequence recognition portion of the construct. Therefore, the probing nucleobase sequence is a sequence of PNA subunits designed to sequence specifically hybridize to a target sequence wherein the presence, absence and/or amount of target sequence can be used to detect the presence, absence and/or number of organisms of interest in a sample. Consequently, with due consideration of the requirements of a PNA probe for the assay format chosen, the length of the probing nucleobase sequence of the PNA probe will generally be chosen such that a stable complex is formed with the target sequence under suitable hybridization conditions or suitable in-situ hybridization conditions.

The probing nucleobase sequence suitable for detecting the target organism listed in Table 1, will generally, but not necessarily, have a length of 18 or fewer PNA subunits wherein the exact nucleobase sequence can be at least 90% homologous to the probing nucleobase sequences listed in Table 1, or their complements. The PNA probes can be 100% homologous to said sequences or can comprise the exact nucleobase sequences appearing the Table 1. Complements of the probing nucleobase sequence are included since it is possible to prepare or amplify copies of the target sequence wherein the copies are complements of the target sequence and thus, will bind to the complement of the probing nucleobase sequences listed in Table 1. Useful probing nucleobase sequences are listed in Table 1. These probing nucleobase sequences have been shown to be relatively or highly specific for the target organism indicated in the presence of other organisms, including the other species of *Candida* (See information listed in Table 1 and the Examples, below).

A PNA probe of this invention will generally have a probing nucleobase sequence that is complementary to the target sequence. Alternatively, a substantially complementary probing nucleobase sequence might be used since it has been demonstrated that greater sequence discrimination can be obtained when utilizing probes wherein there exists one or more point mutations (base mismatch) between the probe and the target sequence (See: Guo et al., *Nature Biotechnology* 75:331-335 (1997)).

This invention contemplates that variations in the probing nucleobase sequences listed in Table 1 shall provide PNA probes that are suitable for the specific detection of the organisms listed. Common variations include, deletions, insertions and frame shifts. Variation of the probing nucleobase sequences within the parameters described herein are considered to be an embodiment of this invention.

Probe Complexes:

In still another embodiment, two probes are designed to hybridize to the target sequence sought to be detected to thereby generate a detectable signal whereby the probing nucleobase sequence of each probe comprises half or approximately half of the nucleobase sequence required for hybridization to the complete target sequence of the organism sought to be detected in the assay such that the aggregate nucleobase sequence of the two probes forms the probing nucleobase sequence that hybridizes to the target sequence. As a non-limiting example, the probing nucleobase sequences of the two probes might be designed using the assay as described in U.S. Pat. No. 6,027,893, entitled: "Method of identifying a nucleic acid using triple helix formation of adjacently annealed probes" by H. Orum et al., herein incorporated by reference. Using this methodology, the probes that hybridize to the target sequence may or may not be labeled. However, it is the probe complex formed by the annealing of the adjacent probes that is detected. Similar compositions comprised solely of PNA probes have been described in U.S. Pat. No. 6,287,772, herein incorporated by reference.

II. Preferred Embodiments of the Invention:

a. PNA Probes:

In one embodiment, this invention is directed to PNA probes. The PNA probes of this invention are suitable for detecting, identifying and/or quantitating one or more species of *Candida* in a sample. The PNA probes, probe sets, methods and kits of this invention are suitable for the analysis of nucleic acid, whether or not it is present within an organism of interest. Accordingly, this invention can be used for both the analysis of organisms or for the analysis of nucleic acid extracted from or derived from an organism of interest.

With the exception of Seq. Id. Nos. 9 and 10 (See: Table 1 for a list of target organisms), generally the PNA probes comprising the identified probing nucleobase sequences that are specific for a certain species of *Candida*. General characteristics (e.g. length, labels, linkers etc.) of PNA probes suitable for the detection, identification or quantitation of these specific organisms have been previously described herein. Non-limiting examples of probing nucleobase sequences of PNA probes of this invention are listed in Table 1, below. The species of *Candida* that the probing nucleobase sequence is designed to determine has also been identified in Table 1 as the target organism.

The PNA probes of this invention may comprise only a probing nucleobase sequence (as previously described herein) or may comprise additional moieties. Non-limiting examples of additional moieties include detectable moieties (labels), linkers, spacers, natural or non-natural amino acids, peptides, enzymes and/or other subunits of PNA, DNA or RNA. Additional moieties may be functional or non-functional in an assay. Generally however, additional moieties will be selected to be functional within the design of the assay in which the PNA probe is to be used. For example, the PNA probes of this invention can be labeled with one or more detectable moieties or labeled with two or more independently detectable moieties. The independently detectable moieties can be independently detectable fluorophores.

TABLE 1

| Seq. ID. No. | Target Organism | Probing Nucleobase Sequence |
|---|---|---|
| 1 | C. albicans | AGA-GAG-CAG-CAT-GCA |
| 2 | C. albicans | AGA-GAG-CAA-CAT-GCA |
| 3 | C. albicans | ACA-GCA-GAA-GCC-GTG |
| 4 | C. albicans | CAT-AAA-TGG-CTA-CCA-GA |
| 5 | C. albicans | CAT-AAA-TGG-CTA-CCC-AG |
| 6 | C. albicans | ACT-TGG-AGT-CGA-TAG |
| 7 | C. albicans | CCA-AGG-CTT-ATA-CTC-GC |
| 8 | C. albicans | CCC-CTG-AAT-CGG-GAT |
| 9 | C. albicans & C. dubliniesis | GAC-GCC-AAA-GAC-GCC |
| 10 | C. albicans & C. dubliniesis | ATC-GTC-AGA-GGC-TAT-AA |
| 11 | C. dubliniesis | TAG-CCA-GAA-GAA-AGG |
| 12 | C. dubliniesis | CAT-AAA-TGG-CTA-GCC-AG |
| 13 | C. dubliniesis | CTC-CGA-TGT-GAC-TGC-G |
| 14 | C. dubliniesis | TCC-CAG-ACT-GCT-CGG |
| 15 | C. glabrata | TCC-AAG-AGG-TCG-AGA |
| 16 | C. glabrata | GCC-AAG-CCA-CAA-GGA |
| 17 | C. glabrata | GCC-GCC-AAG-CCA-CA |
| 18 | C. glabrata | GGA-CTT-GGG-GTT-AG |
| 19 | C. glabrata | CCG-GGT-GCA-TTC-CA |
| 20 | C. krusei | ATG-TAG-AAC-GGA-ACT-A |
| 21 | C. krusei | GAT-TCT-CGG-CCC-CAT-G |
| 22 | C. parapsilosis | CTG-GTT-CGC-CAA-AAA-G |
| 23 | C. tropicalis | AGT-ACG-CAT-CAG-AAA |

The probes of this invention can be used in in-situ hybridization (ISH) and fluorescence in-situ hybridization (FISH) assays. Excess probe used in an ISH or FISH assay often will be removed so that the detectable moiety of specifically bound probes can be detected above the background signal that results from still present but unhybridized probe. Generally, the excess probe can be washed away after the sample has been incubated with probe for a period of time. However, because certain types of self-indicating probes can generate little or no detectable background, they can be used to eliminate the requirement that excess probe be completely removed (washed away) from the sample.

Unlabeled Non-Nucleic Acid Probes:

The probes of this invention need not be labeled with a detectable moiety to be operable within the scope of this invention. When using the probes of this invention it is possible to detect the probe/target sequence complex formed by hybridization of the probing nucleobase sequence of the probe to the target sequence. For example, a PNA/nucleic acid complex formed by the hybridization of a PNA probing nucleobase sequence to the target sequence could be detected using an antibody that specifically interacts with the complex under antibody binding conditions. Suitable antibodies to PNA/nucleic acid complexes and methods for their preparation and use are described in WIPO Patent Application WO95/17430 and U.S. Pat. No. 5,612,458, herein incorporated by reference.

The antibody/PNA/nucleic acid complex formed by interaction of the α-PNA/nucleic acid antibody with the PNA/nucleic acid complex can be detected by several methods. For example, the α-PNA/nucleic acid antibody could be labeled with a detectable moiety. Suitable detectable moieties have been previously described herein. Thus, the presence, absence and/or quantity of the detectable moiety can be correlated with the presence, absence and/or quantity of the antibody/PNA/nucleic acid complex and the species of Candida to be identified by the probing nucleobase sequence of the PNA probe. Alternatively, the antibody/PNA/nucleic acid complex can be detected using a secondary antibody that is labeled with a detectable moiety. Typically the secondary antibody specifically binds to the α-PNA/nucleic acid antibody under antibody binding conditions. Thus, the presence, absence and/or quantity of the detectable moiety can be correlated with the presence, absence and/or quantity of the antibody/antibody/PNA/nucleic acid complex and the species of Candida to be identified by the probing nucleobase sequence of the probe. As used herein, the term antibody includes antibody fragments that specifically bind to other antibodies or other antibody fragments.

Immobilization of Probes to a Surface:

One or more of the PNA probes of this invention may optionally be immobilized to a surface for the detection of the target sequence of a target organism of interest. PNA probes can be immobilized to the surface using the well known process of UV-crosslinking. A PNA probe can be synthesized on the surface in a manner suitable for deprotection but not cleavage from the synthesis support (See: Weiler, J. et al, Hybridization based DNA screening on peptide nucleic acid (PNA) oligomer arrays, Nucl. Acids Res., 25, 24:2792-2799 (July 1997)). In still another embodiment, PNA probes can be covalently linked to a surface by the reaction of a suitable functional group on the probe with a functional group of the surface (See: Lester, A. et al, "PNA Array Technology": Presented at Biochip Technologies Conference in Annapolis (October 1997)). This method is most advantageous since the PNA probes on the surface will typically be highly purified and attached using a defined chemistry, thereby minimizing or eliminating non-specific interactions.

Methods for the chemical attachment of probes to surfaces generally involve the reaction of a nucleophilic group, (e.g. an amine or thiol) of the probe to be immobilized, with an electrophilic group on the support to be modified. Alternatively, the nucleophile can be present on the support and the electrophile (e.g. activated carboxylic acid) present on the probe. Because native PNA possesses an amino terminus, a PNA will not necessarily require modification to thereby immobilize it to a surface (See: Lester et al., Poster entitled "PNA Array Technology").

Conditions suitable for the immobilization of a PNA probe to a surface will generally be similar to those conditions suitable for the labeling of the polymer. The immobilization reaction is essentially the equivalent of labeling whereby the label is substituted with the surface to which the polymer is to be linked.

Numerous types of surfaces derivatized with amino groups, carboxylic acid groups, isocyantes, isothiocyanates and malimide groups are commercially available. Non-limiting examples of suitable surfaces include membranes, chips (e.g. silicone chips), glass, controlled pore glass, polystyrene particles (beads), silica and gold nanoparticles.

Arrays of PNA Probes or Probe Sets:

Arrays are surfaces to which two or more probes have been immobilized each at a specified position. The probing nucleobase sequence of the immobilized probes can be judiciously chosen to interrogate a sample that may contain nucleic acid from one or more target organisms. Because the location and composition of each immobilized probe is known, arrays can be useful for the simultaneous detection, identification and/or quantitation of nucleic acid from two or more target organisms that may be present in the sample. Moreover, arrays of PNA probes can be regenerated by stripping away any of the hybridized nucleic acid after each assay, thereby providing a means to repetitively analyze numerous samples using the same array. Thus, arrays of PNA probes or PNA probe sets may be useful for repetitive screening of samples for target organisms of interest. The arrays of this invention comprise at least one PNA probe (as described herein) suitable for the detection, identification and/or quantitation of at least one species of *Candida*. Exemplary probing nucleobase sequences for the immobilized PNA probes are listed in Table 1.

b. PNA Probe Sets:

In another embodiment, this invention is directed to a PNA probe set suitable for detecting, identifying and/or quantitating one or more species of *Candida* yeast in a sample of interest wherein at least one of the species sought to be detected with the probe set is selected from the group consisting of: *C. albicans, C. dubliniensis, C. krusei, C. glabrata, C. parapsilosis* and *C. tropicalis*. The general and preferred characteristics of PNA probes suitable for the detection, identification and/or quantitation of these specific yeast species have been previously described herein. Preferred probing nucleobase sequences for the target species are listed in Table 1. The grouping of PNA probes within sets characterized for specific groups of species can be a very useful embodiment of this invention. The PNA probes of this invention can be combined with probes for other yeast or even for organisms other than yeast such as been described in U.S. Pat. No. 6,280,946, herein incorporated by reference, wherein a multiplex assay for both yeast and bacteria has been described using a PNA probe set.

Probe sets of this invention comprise at least one PNA probe but need not comprise only PNA probes. For example, probe sets of this invention may comprise mixtures of PNA probes and nucleic acid probes, provided however that a set comprises at least one PNA probe as described herein. In one embodiment, some of the probes of the set can be blocking probes composed of PNA or nucleic acid. In other embodiments, the probe set can be used to determine organisms other than species of *Candida* in addition to the determination of at least one species of *Candida*.

Table 1 lists several species of *Candida* for which two or more probing nucleobase sequences are identified as being suitable for detecting the identified target organism. Where alternative probing nucleobase sequences exist, it can be advantageous to use a probe set containing the two or more PNA probes to thereby increase the detectable signal in the assay.

One exemplary probe set would comprise probes suitable for determining *C. albicans* wherein two or more of the probes of the set comprise a probing nucleobase sequence selected from the group consisting of: AGA-GAG-CAG-CAT-GCA (Seq. Id. No. 1), AGA-GAG-CAA-CAT-GCA (Seq. Id. No. 2), ACA-GCA-GAA-GCC-GTG (Seq. Id. No. 3), CAT-AAA-TGG-CTA-CCA-GA (Seq. Id. No. 4), CAT-AAA-TGG-CTA-CCC-AG (Seq. Id. No. 5), ACT-TGG-AGT-CGA-TAG (Seq. Id. No. 6), CCA-AGG-CTT-ATA-CTC-GC (Seq. Id. No. 7) and CCC-CTG-AAT-CGG-GAT (Seq. Id. No. 8). A second exemplary probe set can comprise probes suitable for determining *C. albicans* and *C. dubliniensis* wherein the probes of the set comprise a probing nucleobase sequence selected from the group consisting of: GAC-GCC-AAA-GAC-GCC (Seq. Id. No. 9) and ATC-GTC-AGA-GGC-TAT-AA (Seq. Id. No. 10). Still a third exemplary probe set can comprise probes suitable for determining only *C. dubliniensis* wherein at least two the probes of the set comprise a probing nucleobase sequence selected from the group consisting of: TAG-CCA-GAA-GAA-AGG (Seq. Id. No. 11), CAT-AAA-TGG-CTA-GCC-AG (Seq. Id. No. 12), CTC-CGA-TGT-GAC-TGC-G (Seq. Id. No. 13) and TCC-CAG-ACT-GCT-CGG (Seq. Id. No. 14). Yet a fourth exemplary probe set can comprise probes suitable for determining only *C. glabrata* wherein at least two the probes of the set comprise a probing nucleobase sequence selected from the group consisting of: TCC-AAG-AGG-TCG-AGA (Seq. Id. No. 15), GCC-AAG-CCA-CAA-GGA (Seq. Id. No. 16), GCC-GCC-AAG-CCA-CA (Seq. Id. No. 17), GGA-CTT-GGG-GTT-AG (Seq. Id. No. 18) and CCG-GGT-GCA-TTC-CA (Seq. Id. No. 19) Still a fifth exemplary probe set can comprise probes wherein the probing nucleobase sequence is selected from the group consisting of: ATG-TAG-AAC-GGA-ACT-A (Seq. Id. No. 20) and GAT-TCT-CGG-CCC-CAT-G (Seq. Id. No. 21).

In other embodiments, the probe set can comprise two or more probes such that two or more of the species of *Candida* identified herein are detected, identified and/or quantitated. Preferably, the set comprises two or more independently detectable PNA probes wherein each independently detectable probe is suitable for detecting, identifying and/or quantitating a particular species of *Candida*. For example, a PNA probe set comprising Seq. Id. Nos. 1 and 11, wherein each probe is labeled with an independently detectable moiety and can be used in two independent assays, or a single multiplex assay, for the independent determination of both *C. albicans* and *C. dubliniensis* (See: Example 2 for a non-multiplex assay demonstrates that these species can be independently determined using the probing nucleobase sequences identified herein).

c. Methods:

In another embodiment, this invention is directed to a method suitable for detecting, identifying and/or quantitating one or more species of *Candida* in a sample of interest. According to the method, one or more individual species of *Candida* can be determined. The general and preferred characteristics of PNA probes suitable for the detection, identification and/or quantitation of these target organisms have been previously described herein. Exemplary probing nucleobase sequences are listed in Table 1.

In one embodiment, the method can comprise contacting the sample with one or more PNA probes, wherein suitable probes have been previously described herein. According to the method, the presence, absence and/or number of the one or more species of *Candida* in the sample can be detected, identified and/or quantitated by correlating hybridization of the probing nucleobase sequence of one or more PNA probes to the target sequence of a target organism of interest under suitable hybridization conditions or suitable in-situ hybridization conditions. The grouping of PNA probes within probe sets to be used with methods for detecting specific organisms or groups of organisms can also be done. Exemplary probes and probe sets suitable for the practice of this method have been previously described herein. Preferred methods for the determination of yeast, with or without the simultaneous detection of bacteria, have been previously described in U.S. Pat. No. 6,280,946, incorporated herein by reference. Examples 1 and 2, below, provide further methods for the determination of the specific yeast identified herein.

Exemplary Assay Formats:

The probes, probe sets, methods and kits of this invention can be used for the detection, identification and/or quantitation of *Candida* yeast. In-situ hybridization (ISH) or fluorescent in-situ hybridization (FISH) can be used as the assay format: for detecting, identifying and/or quantitating target organisms. Specific PNA-RSH methods used to experimentally test specific PNA probes can be found in Examples 1 and 2 of this specification. The examples contained herein demonstrate that labeled PNA probes comprising the probing nucleobase sequences listed in Table 1 are specific for determining target organisms even when other organisms listed in the Table are present in the assay. The experimental conditions used in the Examples yield results within approximately 1-4 hours. The identical experimental protocol was found to be specific, reliable and generally applicable regardless of the nature or sequence of the PNA probes used.

Organisms that have been treated with the PNA probes or probe sets or kits described herein can be determined by several exemplary methods. The cells can be fixed on slides and visualized with a film, camera, slide scanner or microscope. Alternatively, the cells can be fixed and then analyzed in a flow cytometer. Slide scanners and flow cytometers are particularly useful for rapidly quantitating the number of target organisms present in a sample of interest.

d. Kits:

In yet another embodiment, this invention is directed to kits suitable for performing an assay that detects the presence, absence and/or quantity of *Candida* yeast in a sample. The general and preferred characteristics of PNA probes suitable for the detection, identification and/or quantitation of *Candida* have been previously described herein. Exemplary probing nucleobase sequences are listed in Table 1. Furthermore, methods suitable for using the PNA probes or PNA probe sets of a kit suitable to detect, identify and/or quantitate target organisms in a sample of interest have been previously described herein.

The kits of this invention comprise one or more PNA probes and other reagents or compositions that are selected to perform an assay or otherwise simplify the performance of an assay. The kits can, for example, comprise buffers and/or other reagents useful for performing a PNA-ISH or PNA-FISH assay. In other embodiments, the buffers and/or other reagents can be useful for performing a nucleic acid amplification reaction such as a PCR reaction.

In kits that contain sets of probes, wherein each of at least two probes of the set are used to detect different species of *Candida*, the probes of the set can be labeled with one or more independently detectable moieties so that each specific target organism can be individually detected, identified and/or quantitated in a single assay (e.g. a multiplex assay).

e. Exemplary Applications for Using the Invention:

Whether support bound or in solution, the PNA probes, probe sets, methods and kits of this invention can be useful for the rapid, sensitive and reliable detection of *Candida* yeast in food, beverages, water, pharmaceutical products, personal care products, dairy products or for the analysis of environmental samples. The analysis of beverages can include soda, bottled water, fruit juice, beer, wine or liquor products. Suitable PNA probes, probe sets, methods and kits of this invention can be particularly useful for the analysis of raw materials, equipment, products or processes used to manufacture or store food, beverages, water, pharmaceutical products, personal care products, dairy products or for the analysis of environmental samples.

Whether support bound or in solution; the PNA probes, probe sets, methods and kits of this invention are can be useful for the detection of *Candida* yeast in clinical samples and clinical environments. By way of a non-limiting example, the PNA probes, probe sets, methods and kits of this invention can be particularly useful in the analysis of blood culture samples. Other non-limiting examples of clinical samples include: sputum, laryngeal swabs, gastric lavage, bronchial washings, biopsies, aspirates, expectorates, body fluids (e.g. spinal, pleural, pericardial, synovial, blood, pus, amniotic, and urine), bone marrow and tissue sections. Suitable PNA probes, probe sets, methods and kits can also be particularly useful for the analysis of clinical specimens, equipment, fixtures or products used to treat humans or animals.

EXAMPLES

This invention is now illustrated by the following examples that are not intended to be limiting in any way.

All PNA oligomers were prepared using conventional synthesis and purification procedures.

Example 1

Analysis of a PNA Probe Specific to *Candida albicans*

```
PNA Probe sequence
Can26S03/Flu      Flu-O-AGAGAGCAGCATGCA-NH2
```
Note:
Flu = 5(6)-carboxy-fluorescein;
O = 8-amino-3,6-dioxaoctanoic acid Reference Strains and Clinical Isolates. Fourteen *C. albicans* reference strains and nineteen other reference strains representing phylogenetically related *Candida* species and *Lodderomyces elongisporus*, mainly within the *C. albicans* clade, were selected from the Agricultural Research Service Culture Collection (NRRL) Peoria, Ill. One *Saccharomyces cerevisiae* strain was obtained from the American Type Culture Collection (ATCC), Manassas, Va. Fifty-eight *C. dubliniensis* and thirty-nine *C. albicans* clinical isolates were collected, at the Institute of Medical Microbiology, University Hospital, Aachen, Germany. The *C. dubliniensis* isolates were mainly from HIV-positive patients and from respiratory specimens of patients with cystic fibrosis. Clinical isolates of *C. albicans* were from various clinical specimens, including blood cultures, and chosen to represent different strains, i.e. serotype A, the biovar *stellatoidea* as well as phenotypically aberrant isolates such as red pigment strain and strains that failed to assimilate glucosamine and N-acetylglucosamine. All strains and isolates were identified by D1/D2 26S rDNA sequence analysis. For PNA FISH analysis, reference strains and clinical isolates were inoculated into yeast-malt (YM) broth (Difco Laboratories, Detroit, Mich.) and incubated overnight at 35° C. Furthermore, thirty-three *C. albicans* isolates and eighteen other isolates representing clinically significant yeast species obtained from various clinical specimens, including blood cultures (Clinical Microbiology Laboratory, Cleveland Clinic Foundation, OH), were spiked into FAN BacT/Alert medium (Organon Teknika, Durham, N.C.) and incubated in the BacT/Alert Microbial detection system (Organon Teknika) until they were detected as positive by the system. The eighteen non-*C. albicans* isolates comprised *C. glabrata* (n=5), *C. tropicalis* (n=3), *C. krusei* (n=2), *C. parapsilosis* (n=4), *C. lusitaniae* (n=3), and *C. zeylanoides* (n=1).

Clinical Specimens. A total of thirty-three yeast-positive blood culture bottles (FAN BacT/Alert, Organon Teknika) from routine testing at the Clinical Microbiology Laboratory, Cleveland Clinic Foundation, OH were included in this study. In addition, twenty-five simulated yeast-positive blood culture bottles (FAN BacT/Alert, Organon Teknika) were made by inoculating routine blood culture bottles that were negative following 7 days incubation. The inoculation was done with just a few colony-forming units of strains representing clinically significant non-*C. albicans* species and comprised *C. glabrata* (n=2), *C. lusitaniae* (n=4), *C. tropicalis* (n=4), *C. guilliermondii* (n=1) *C. krusei* (n=3), *C. parapsilosis* (n=4), *C. famata* (n=2), *C. norvegensis* (n=4), and *C. neoformans* (n=1). These strains included reference strains from ATCC and the German Collection of Microorganisms and Cell. Cultures, Braunschweig, Germany (DSM) as well as recent clinical isolates from the Institute of: Medical Microbiology, University Hospital RWTH Aachen, Aachen, Germany. The blood culture bottles were re-incubated in the BacT/Alert Microbial detection system (Organon Teknika) until they were detected as positive by the system.

Preparation of Smears. One drop of phosphate-buffered saline (PBS) was placed in the well of a Teflon-coated microscope slide (Clear Coat, Erie Scientific, Portsmouth, N.H.) and 10-25 µL of culture or a small drop was added, mixed and spread throughout the well. The smear was fixed by either placing the slide on an 80° C. slide warmer for 2 hours or at 60° C. for 20 minutes. The slide was subsequently immersed into 95% ethanol for 1-2 minutes and allowed to air-dry.

Fluorescence In Situ Hybridization Using PNA Probes (PNA FISH). Smears were covered with approximately 20 µL of hybridization solution containing 10% (w/v) dextran sulfate (Sigma Chemical Co., St. Louis, Mo.), 10 mM NaCl, 30% (v/v) formamide (Sigma), 0.1% (w/v) sodium pyrophosphate (Sigma), 0.2% (w/v) polyvinylpyrrolidone (Sigma), 0.2% (w/v) ficoll (Sigma), 5 mM $Na_2EDTA$ (Sigma), 0.1% (v/v) Triton X-100 (Aldrich), 50 mM Tris/ HCl pH 7.5 and 250 nM fluorescein-labeled PNA probe targeting *C. albicans*. Coverslips were placed on the smears to ensure even coverage with hybridization solution, and the slides were placed on a slide warmer with a humidity chamber (Slidemoat, Boeckel, Germany) and incubated for 90 min at 55° C. Following hybridization, the coverslips were removed by submerging the slides into approximately 20 ml/slide pre-warmed 5 mM Tris, pH 10, 15 mM NaCl (J. T. Baker), 0.1% (v/v) Triton X-100 (Aldrich) in a water bath at 55° C. and washed for 30 min. The slides were then air-dried. Each smear was finally mounted using one drop of IMAGEN Mounting Fluid (DAKO, Ely, UK) and covered with a coverslip. Microscopic examination was conducted using a fluorescence microscope (Optiphot, Nikon Corporation, Tokyo, Japan) equipped with a 60×/1.4 oil objective (Nikon), an HBO 100 W mercury lamp, and a FITC/Texas Red dual band filter set (Chroma Technology Corp., Brattleboro, Vt.).

Results

The probe was tested on a panel of reference strains representing *C. albicans* and other *Candida* species, including phylogentically closely related *Candida* species, clinically relevant *Candida* species and other yeast species. The results are summarized in Table 2 and show that the probe is highly specific.

TABLE 2

Results for reference strains analyzed by PNA FISH with *C. albicans*-specific PNA probe

| Yeast species | Strain ID | Can26S03/Flu |
|---|---|---|
| Candida albicans | NRRL Y-107 | + |
| Candida albicans | NRRL Y-12983 | + |
| Candida albicans | NRRL Y-17967 | + |
| Candida albicans | NRRL Y-17968 | + |
| Candida albicans | NRRL Y-17974 | + |
| Candida albicans | NRRL Y-17976 | + |
| Candida albicans | NRRL Y-302 | + |
| Candida albicans | NRRL Y-477 | + |
| Candida albicans | NRRL Y-6359 | + |
| Candida albicans | NRRL Y-6943 | + |
| Candida albicans | NRRL Y-79 | + |
| Candida albicans | NRRL Y-81 | + |
| Candida albicans | NRRL Y-82 | + |
| Candida albicans | NRRL YB-3898 | + |
| Candida dubliniensis | NRRL Y-17841 | − |
| Candida dubliniensis | NRRL Y-17512 | − |
| Candida dubliniensis | NRRL Y-17969 | − |
| Candida dubliniensis | NRRL Y-17971 | − |
| Candida dubliniensis | NRRL Y-17972 | − |
| Candida dubliniensis | NRRL Y-17973 | − |
| Candida glabrata | NRRL Y 65 | − |
| Candida maltosa | NRRL Y-17677 | − |
| Candida tropicalis | NRRL Y-12968 | − |
| Candida tropicalis | NRRL Y-1552 | − |
| Candida tropicalis | NRRL Y-5716 | − |
| Candida viswanathii | NRRL Y-6660 | − |
| Candida lodderae | NRRL Y-17317 | +/− |
| Candida parapsilosis | NRRL Y-12969 | − |
| Candida parapsilosis | NRRL Y-543 | − |
| Candida sojae | NRRL Y-17909 | − |
| Lodderomyces elongisporus | NRRL YB-4239 | − |
| Lodderomyces elongisporus | NRRL Y-7681 | − |
| S. cerevisiae | ATCC 4098 | − |

This is to our knowledge the first probe targeting rRNA that has been shown not to react with *C. dubliniensis*, a recently discovered *Candida* species that is often misidentified as *C. albicans* using standard methods, such as germ tube analysis and carbon assimilation methods.

The sensitivity and specificity of the *C. albicans* PNA FISH were further examined using one hundred forty-eight clinical isolates representing *C. albicans* and other clinically relevant yeast species. The results are summarized in Table 3. The assay correctly identified all *C. albicans* isolates and gave negative results with all other isolates.

TABLE 3

Reaction of *C. albicans* PNA FISH with 148 isolates representing clinically relevant yeast species.

| Species | C. albicans PNA FISH | |
|---|---|---|
| | Positive (n) | Negative (n) |
| Candida albicans | 72 | 0 |
| Candida dubliniensis | 0 | 58 |
| Candida glabrata | 0 | 5 |
| Candida tropicalis | 0 | 3 |
| Candida krusei | 0 | 2 |
| Candida parapsilosis | 0 | 4 |
| Candida lusitaniae | 0 | 3 |
| Candida zeylanoides | 0 | 1 |

The diagnostic performance of *C. albicans* PNA FISH was evaluated directly on 33 yeast-positive blood culture bottles as compared to results obtained by standard methods. These comprised nine *C. albicans* cultures and twenty-four non-*C. albicans* cultures representing six to seven different species. The specificity was furthermore tested with twenty-five simulated blood culture bottles representing nine different species. The results are summarized in Table 4 and show 100% agreement with standard methods supporting a 100% diagnostic sensitivity and 100% diagnostic specificity.

TABLE 4

Reaction of *C. albicans* PNA FISH with yeast-positive blood cultures comprising 33 real blood culture bottles and 25 artificially spiked blood culture bottles.

| Identification | C. albicans PNA FISH | |
|---|---|---|
| | Positive (n) | Negative (n) |
| Candida albicans | 9 | 0 |
| Candida glabrata | 0 | 11 |
| Candida parapsilosis | 0 | 10 |
| Candida tropicalis | 0 | 5 |
| Candida krusei | 0 | 4 |
| Candida lusitaniae | 0 | 9 |
| Candida famata | 0 | 2 |
| Candida norvegensis | 0 | 4 |
| Candida guilliermondii | 0 | 1 |
| Cryptococcus neoformans | 0 | 2 |
| Other yeast, not identified | 0 | 1 |

Summary

PNA FISH using PNA probes targeting rRNA of *C. albicans* was used for identification of *C. albicans* in yeast positive blood culture bottles in a time frame not possible using conventional methods. The test was performed on smears made directly from the blood culture bottles and interpretation of results was conducted by microscopy, such that the PNA FISH procedure simply added the high specificity of PNA probes to standard microbiological procedures (i.e. smear preparation and microscopy) to provide definitive identification.

The *C. albicans* specific PNA probe showed a very high degree of specificity, not only when tested with clinical isolates, but also when further challenged with strains from the *C. albicans* clade. These findings are ascribed to the high specificity of PNA probes combined with the use of the D1/D2 region of 26S rRNA as target; a region that has been used for systematic studies of yeasts. These data are yet another example of how molecular diagnostic methods using rRNA sequences as target can replace classic phenotypically based microbiological identification methods. In fact, several atypical *C. albicans* strains were correctly identified by *C. albicans* PNA FISH.

*C. albicans* PNA FISH provides rapid and specific identification of *C. albicans*. No confirmation testing is required for identification, thus allowing the appropriate patient treatment to be administered more quickly, i.e. immediate treatment with fluconazole since almost all isolates of *C. albicans* are susceptible to this drug.

Example 2

PNA Probes that Distinguish Between *C. dubliniensis* and *C. albicans*

```
Probe sequence
Can18S09/Flu    Flu-O-EE-TAGCCAGAAGAAAGG-EE-NH2
                (C. dubliniensis)

Can26S05/Flu    Flu-O-EE-ACAGCAGAAGCCGTG-EE-NH2
                (C. albicans)
```

Note: E=compound having the formula:

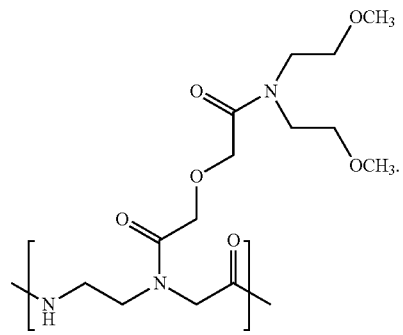

Reference Strains. Reference strains were obtained from Agricultural Research Service Culture Collection (NRRL) Peoria, Ill. The strains were propagated in yeast and mold broth (Difco Laboratories, Detroit, Mich.) at 30-35° C.

Preparation of Smears. One drop of phosphate-buffered saline (PBS) was placed in the well of a Teflon-coated microscope slide (Clear Coat, Erie Scientific, Portsmouth, N.H.) and 10 μL of culture was added, mixed and spread throughout the well. The smear was fixed by either placing the slide on an 80° C. slide warmer for 2 hours or by flame-fixation by passing the slides through the blue cone of a Bunsen burner. The slide was subsequently immersed into 95% ethanol for 1-2 minutes and allowed to air-dry.

Fluorescence In Situ Hybridization Using PNA Probes (PNA FISH). Smears were covered with approximately 10 μL of hybridization solution containing 10% (w/v) dextran sulfate (Sigma Chemical Co., St. Louis, Mo.), 10 nM NaCl, 30% (v/v) formamide (Sigma), 0.1% (w/v) sodium pyrophosphate (Sigma), 0.2% (w/v) polyvinylpyrrolidone (Sigma), 0.2% (w/v) ficoll (Sigma), 5 mM Na$_2$EDTA (Sigma), 0.1% (v/v) Triton X-100 (Aldrich), 50 mM Tris/HCl pH 7.5 and 100 nM fluorescein-labeled PNA probe targeting *C. albicans* or 500 nM fluorescein-labeled PNA probe targeting *C. dubliniensis*. Coverslips were placed on the smears to ensure even coverage with hybridization solution, and the slides were placed on a slide warmer with a humidity chamber (Slidemoat, Boeckel, Germany) and incubated for 30 min at 50° C. Following hybridization, the coverslips were removed by submerging the slides into approximately 20 mL/slide pre-warmed 5 mM Tris, pH 10, 15 mM NaCl (J. T. Baker), 0.1% (v/v) Triton X-100 (Aldrich) in a water bath at 50° C. and washed for 30 min. The slides were then air-dried. Each smear was finally mounted using one drop of IMAGEN Mounting Fluid (DAKO, Ely, UK) and covered with a coverslip. Microscopic examination was conducted using a fluorescence microscope (Optiphot, Nikon Corporation, Tokyo, Japan) equipped with a 60×/1.4 oil objective (Nikon), an HBO 100 W mercury lamp, and a FITC/Texas Red dual band filter set (Chroma Technology Corp., Brattleboro, Vt.).

Results

Fifteen *C. albicans* and six *C. dubliniensis* reference strains were tested with the PNA FISH assay The results are summarized in Table 5. Of the fifteen *C. albicans* strains, 15 (100%) produced a positive result with the *C. albicans* PNA probe and a negative result with the *C. dubliniensis* PNA probe. Of the six *C. dubliniensis* strains, six (100%) produced a negative result with the *C. albicans* PNA probe and a positive result with the *C. dubliniensis* PNA probe.

TABLE 5

Results for reference strains analyzed by PNA FISH with *C. albicans* and *C. dubliniensis* PNA probes

| Organism | Strain ID | Can18S05/Flu | Can23S09/Flu |
|---|---|---|---|
| C. albicans | NRRL Y-12983 | + | − |
| C. albicans | NRRL Y-79 | + | − |
| C. albicans | NRRL Y-81 | + | − |
| C. albicans | NRRL Y-82 | + | − |
| C. albicans | NRRL Y-107 | + | − |
| C. albicans | NRRL Y-302 | + | − |
| C. albicans | NRRL Y-477 | + | − |
| C. albicans | NRRL Y-6359 | + | − |
| C. albicans | NRRL Y-6943 | + | − |
| C. albicans | NRRL Y-17967 | + | − |
| C. albicans | NRRL Y-17968 | + | − |
| C. albicans | NRRL Y-17974 | + | − |
| C. albicans | NRRL Y-17975 | + | − |
| C. albicans | NRRL Y-17976 | + | − |
| C. albicans | NRRL YB-3898 | + | − |
| C. dubliniensis | NRRL Y-17841 | − | + |
| C. dubliniensis | NRRL Y-17512 | − | + |
| C. dubliniensis | NRRL Y-17969 | − | + |
| C. dubliniensis | NRRL Y-17971 | − | + |
| C. dubliniensis | NRRL Y-17972 | − | + |
| C. dubliniensis | NRRL Y-17973 | − | + |

Summary

*C. dubliniensis* shares many phenotypical characteristics with *C. albicans* and is therefore incorrectly identified as *C. albicans* by current standard methods, such as germ tube analysis and commercially available carbon assimilation tests. We have here shown that PNA FISH using PNA probes targeting rRNA of *C. dubliniensis* and *C. albicans* is a 100% accurate method for the differentiation of *C. albicans* and *C. dubliniensis*.

Example 3

Analysis of a PNA Probe Specific to *Candida glabrata*

```
PNA Probe sequence
Can18S11/Flu    Flu-O-TCCAAGAGGTCGAGA-NH2

EuUni/Cy3       Cy3-OO-ACC-AGA-CTT-GCC-CTC-NH2
```
Note:
Cy3 = the cyanine 3 dye available from Amersham Pharmacia Biotech.

Reference Strains. Reference strains were obtained from Agricultural Research Service Culture Collection (NRRL) Peoria, Ill. and American Type Culture Collection ATCC), Manassas, Va. The strains were propagated in yeast and mold broth (Difco Laboratories, Detroit, Mich.) at 30-35° C.

Clinical Specimens. A total of seventeen yeast-positive blood culture bottles (FAN BacT/Alert, Organon Teknika) from routine testing at the Clinical Microbiology Laboratory, Cleveland Clinic Foundation, OH were included in this study.

Preparation of Smears. One drop of phosphate-buffered saline (PBS) was placed in the well of a Teflon-coated microscope slide (Clear Coat, Erie Scientific, Portsmouth, N.H.) and 10 μL of culture was added, mixed and spread throughout the well. The smear was fixed by either placing the slide on an 80° C. slide warmer for 2 hours or at 60° C. for 60 minutes. The slide was subsequently immersed into 95% ethanol for 1-2 minutes and allowed to air-dry.

Fluorescence In Situ Hybridization Using PNA Probes (PNA FISH). Smears were covered with approximately 5-10 μL of hybridization solution containing 10% (w/v) dextran sulfate (Sigma Chemical Co., St. Louis, Mo.), 10 mM NaCl, 30% (v/v) formamide (Sigma), 0.1% (w/v) sodium pyrophosphate (Sigma), 0.2% (w/v) polyvinylpyrrolidone (Sigma), 0.2% (w/v) ficoll (Sigma), 5 mM $Na_2EDTA$ (Sigma), 0.1% (v/v) Triton X-100 (Aldrich), 50 mM Tris/HCl pH 7.5 and 250 nM fluorescein-labeled PNA probe targeting *C. glabrata* and 1 nM Cy3-labeled PNA probe targeting eukarya. EuUni/Cy3 was added in low conc. to give non-detected cells a reddish appearance. Coverslips were placed on the smears to ensure even coverage with hybridization solution, and the slides were placed on a slide warmer with a humidity chamber (Slidemoat, Boeckel, Germany) and incubated for 90 min at 55° C. Following hybridization, the coverslips were removed by submerging the slides into approximately 20 mL/slide pre-warmed 5 mM Tris, pH 10, 15 mM NaCl (J. T. Baker), 0.1% (v/v) Triton X-100 (Aldrich) in a water bath at 55° C. and washed for 30 min. The slides were then air-dried. Each smear was finally mounted using one drop of IMAGEN Mounting Fluid (DAKO, Ely, UK) and covered with a coverslip. Microscopic examination was conducted using a fluorescence microscope (Optiphot, Nikon Corporation, Tokyo, Japan) equipped with a 60×/1.4 oil objective (Nikon), an HBO 100 W mercury lamp, and a FITC/Texas Red dual band filter set (Chroma Technology Corp., Brattleboro, Vt.).

Results

The probe was tested on a panel of reference strains representing *C. glabrata* and other *Candida* species, including phylogentically closely related *Candida* species, clinically relevant *Candida* species and other yeast species. The results are summarized in Table 6 and show that the probe is highly specific.

TABLE 6

Results for reference strains analyzed by PNA FISH with *C. glabrata*-specific PNA probe

| Yeast species | Strain ID | Can18S11/Flu |
|---|---|---|
| *Candida glabrata* | NRRL Y 65 | + |
| *Candida glabrata* | NRRL Y-2242 | + |
| *Candida glabrata* | NRRL YB-3659 | + |
| *Candida glabrata* | NRRL YB-3660 | + |
| *Candida glabrata* | NRRL YB-4389 | + |
| *Candida glabrata* | NRRL YB-4319 | + |
| *Candida glabrata* | NRRL YB-1333 | + |
| *Candida glabrata* | NRRL Y-1418 | + |
| *Candida glabrata* | NRRL YB-4018 | + |
| *Candida albicans* | NRRL Y-17968 | − |
| *Candida albicans* | NRRL Y-17976 | − |
| *Candida albicans* | NRRL Y-302 | − |
| *Candida albicans* | NRRL Y-79 | − |
| *Candida albicans* | NRRL Y-81 | − |
| *K. delphensis* | NRRL Y-2379 | − |
| *K. bacillisporus* | NRRL Y-17846 | − |
| *S. cerevisiae* | ATCC 4098 | − |

The diagnostic performance of *C. glabrata*. PNA FISH was evaluated directly on seventeen yeast-positive blood culture bottles as compared to results obtained by standard methods. These comprised four *C. glabrata* cultures and thirteen non-*C. glabrata* cultures representing four to five different species. The results are summarized in Table 7 and show 100% agreement with standard methods supporting a 100% diagnostic sensitivity and 100% diagnostic specificity.

TABLE 7

Reaction of *C. glabrata* PNA FISH with seventeen routine yeast-positive blood cultures.

| Identification | *C. glabrata* PNA FISH | |
|---|---|---|
| | Positive (n) | Negative (n) |
| *Candida albicans* | 0 | 8 |
| *Candida glabrata* | 4 | 0 |
| *Candida parapsilosis* | 0 | 2 |
| *Candida tropicalis* | 0 | 1 |
| *Candida lusitaniae* | 0 | 1 |
| Other yeast, not identified | 0 | 1 |

Having described preferred embodiments of the invention, it will now become apparent to one of skill in the art that other embodiments incorporating the concepts may be used. It is felt, therefore, that these embodiments should not be limited to disclosed embodiments but rather should be limited only by the spirit and scope of the invention.

We claim:

1. A PNA probe set suitable for detecting, identifying or quantitating one or more species of *Candida* yeast in a sample, wherein the probe set comprises PNA probes with probing nucleobase sequences consisting of: AGA-GAG-CAG-CAT-GCA (Seq. Id. No. 1), AGA-GAG-CAA-CAT-GCA (Seq. Id. No. 2), ACA-GCA-GAA-GCC-GTG (Seq. Id. No. 3), CAT-AAA-TGG-CTA-CCA-GA (Seq. Id. No. 4), CAT-AAA-TGG-CTA-CCC-AG (Seq. Id. No. 5), ACT-TGG-AGT-CGA-TAG (Seq. Id. No. 6), CCA-AGG-CTT-ATA-CTC-GC (Seq. Id. No. 7), and CCC-CTG-AAT-CGG-GAT (Seq. Id. No. 8), or their complements.

2. The probe set of claim 1, wherein at least one probe of the set is unlabeled.

3. The probe set of claim 1, wherein at least one probe is labeled with a detectable moiety.

4. The probe set of claim 3, wherein the detectable moiety or moieties are selected from the group consisting of: a dextran conjugate, a branched nucleic acid detection system, a chromophore, a fluorophore, a spin label, a radioisotope, an enzyme, a hapten, an acridinium ester and a chemiluminescent compound.

5. The probe set of claim 1, wherein all the probes of the set are labeled with one or more detectable labels.

6. The probe set of claim 1, wherein two or more probes are independently detectable.

7. The probe set of claim 1, wherein at least one probe of the set is self-indicating.

8. The probe set of claim 1, wherein at least one probe of the set is support bound.

9. A kit suitable for performing an assay that determines the presence, absence or quantity of one or more species of *Candida* yeast in a sample, wherein said kit comprises:
   a) a combination of PNA probes, wherein the PNA probes comprise probing nucleobase sequences consisting of: AGA-GAG-CAG-CAT-GCA (Seq. Id. No. 1), AGA-GAG-CAA-CAT-GCA (Seq. Id. No. 2), ACA-GCA-GAA-GCC-GTG (Seq. Id. No. 3) , CAT-AAA-TGG-CTA-CCA-GA (Seq. Id. No. 4) , CAT-AAA-TGG-CTA-CCC-AG (Seq. Id. No. 5) , ACT-TGG-AGT-CGA-TAG (Seq. Id. No. 6) , CCA-AGG-CTT-ATA-CTC-GC (Seq. Id. No. 7) , and CCC-CTG-AAT-CGG-GAT (Seq. Id. No. 8), or their complements; and
   b) other reagents or compositions necessary to perform the assay.

10. The kit of claim 9, further comprising an antibody or antibody fragment which specifically binds to the PNA/nucleic acid complex.

11. The kit of claim 10, wherein the antibody is labeled with a detectable moiety.

12. The kit of claim 11, wherein the detectable moiety is selected from the group consisting of: a dextran conjugate, a branched nucleic acid detection system, a chromophore, a fluorophore, a spin label, a radioisotope, an enzyme, a hapten, an acridinium ester and a chemiluminescent compound.

13. The kit of claim 9, further comprising buffers and/or other reagents suitable for performing a PNA-ISH or PNA-FISH assay.

14. The kit of claim 9, wherein the PNA probes of the kit are unlabeled.

15. The kit of claim 9, wherein at least one PNA probe is labeled with a detectable moiety.

16. The kit of claim 9, wherein two or more PNA probes are labeled with independently detectable moieties.

17. The kit of claim 16, wherein the independently detectable moieties are independently detectable fluorophores.

18. The kit of claim 9, wherein at least one PNA probe is labeled with at least two independently detectable moieties.

19. The kit of claim 9, further comprising buffers and/or other reagents suitable for performing a nucleic acid amplification reaction.

20. The kit of claim 9, wherein at least one PNA probe is self-indicating.

* * * * *